(12) United States Patent
Eichmann

(10) Patent No.: US 12,152,226 B2
(45) Date of Patent: Nov. 26, 2024

(54) CELL CULTURE BOTTLE

(71) Applicant: Green Elephant Biotech GmbH, Giessen (DE)

(72) Inventor: Joel Eichmann, Giessen (DE)

(73) Assignee: GREEN ELEPHANT BIOTECH GMBH, Giessen (DE)

( * ) Notice: Subject to any disclaimer, the term of this patent is extended or adjusted under 35 U.S.C. 154(b) by 728 days.

(21) Appl. No.: 17/425,926

(22) PCT Filed: Jan. 17, 2020

(86) PCT No.: PCT/EP2020/051093
§ 371 (c)(1),
(2) Date: Jul. 26, 2021

(87) PCT Pub. No.: WO2020/152038
PCT Pub. Date: Jul. 30, 2020

(65) Prior Publication Data
US 2022/0177817 A1    Jun. 9, 2022

(30) Foreign Application Priority Data

Jan. 25, 2019 (EP) .................. 19153761

(51) Int. Cl.
| C12M 1/24 | (2006.01) |
| C12M 1/00 | (2006.01) |
| C12M 1/26 | (2006.01) |
| C12M 3/04 | (2006.01) |

(52) U.S. Cl.
CPC ............ *C12M 23/08* (2013.01); *C12M 23/20* (2013.01); *C12M 27/12* (2013.01); *C12M 33/16* (2013.01)

(58) Field of Classification Search
None
See application file for complete search history.

(56) References Cited

U.S. PATENT DOCUMENTS

2008/0206735 A1 *  8/2008  Asgari ................ C12M 23/08
435/395

FOREIGN PATENT DOCUMENTS

| DE | 102005062052 A1 * | 6/2007 | ......... B01F 11/0094 |
| EP | 0244873 A2 | 11/1987 | |
| EP | 1304370 A1 | 4/2003 | |
| WO | 2008104586 A2 | 9/2008 | |
| WO | 2020152038 A1 | 7/2020 | |

OTHER PUBLICATIONS

European Patent Office, International Search Report and Written Opinion for PCT Application No. PCT/EP2020/051093, mail date May 4, 2020.

* cited by examiner

*Primary Examiner* — William H. Beisner
(74) *Attorney, Agent, or Firm* — SoCal IP Law Group LLP; Angelo Gaz

(57) ABSTRACT

The invention relates to a cell culture bottle for adherent cells (e.g. human mesenchymal stem cells), comprising: a vessel; an internal cylinder, which has an internal Archimedes screw; an internal central tube, through which liquid can flow; and at least one wall arranged around the central tube. This arrangement provides an enlarged inner surface for the growth of the cells and for the reliable mixing of the fluid. The cell culture bottle is formed as a single piece and can be simply and economically produced as a disposable device by means of additive manufacturing.

11 Claims, 5 Drawing Sheets

Figure 1:
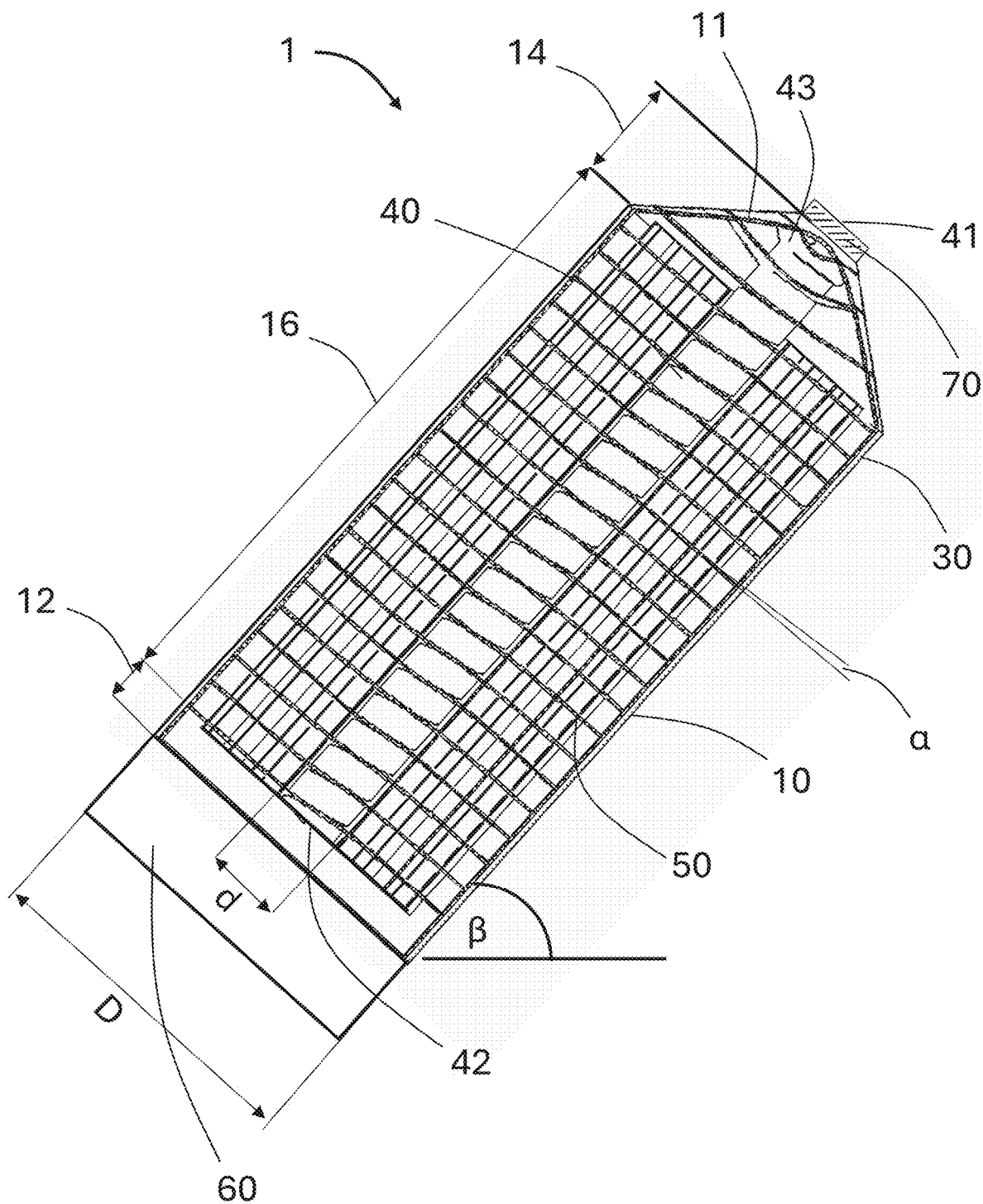

Fig. 3a
Fig. 3b
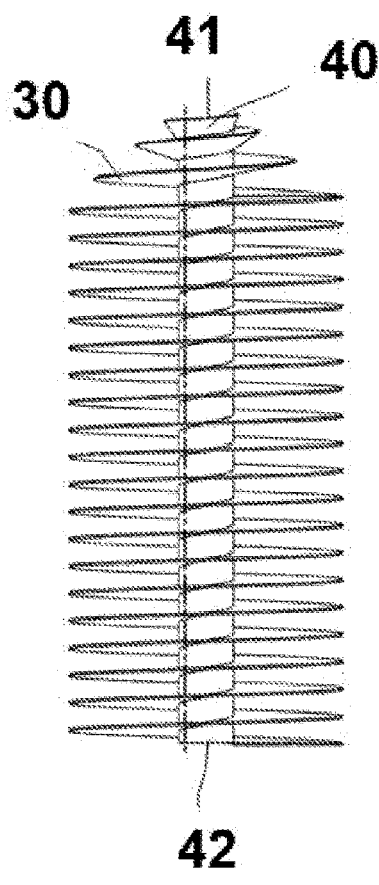
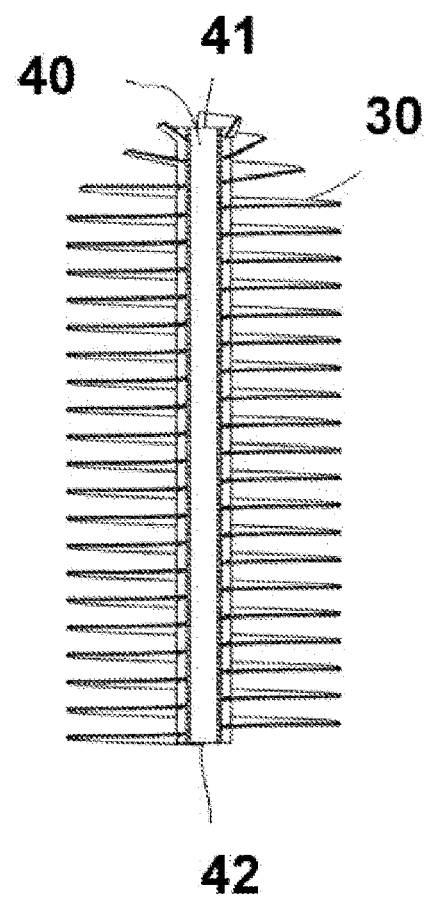

CELL CULTURE BOTTLE

RELATED APPLICATION INFORMATION

This patent claims priority from International PCT Patent Application No. PCT/EP2020/051093, filed Jan. 17, 2020, entitled, "CELL CULTURE BOTTLE", which claims priority to European Patent Application No. EP 19153761.2, filed Jan. 25, 2019, all of which are incorporated herein by reference in their entirety.

The present invention relates to an apparatus and a method for culturing cells. The apparatus is a roller bottle having an improved surface-to-volume ratio in which it is possible at the same time to culture more cells. Cell cultures are widely used in biological and medical research. By means of cell culture, various biological substances, such as proteins or antibodies, can be produced in large quantities. This is important for vaccine production, diagnostics and immunological analysis.

DESCRIPTION AND INTRODUCTION OF THE GENERAL FIELD OF THE INVENTION

Cell culture refers to the culturing of cells in a suitable growth medium outside of a living organism. The cells can be of human or animal origin, can originate from plants, algae or fungi, or can be microalgae or bacteria. The cells can also be tumor cells, or cells, or cells that have been genetically modified (e.g., by introduction of a plasmid as a vector).

Cell lines are cells of a tissue type that propagate by continually dividing. A person skilled in the art is familiar with non-immortalized cell lines which have only a limited division rate and is familiar with immortalized cell lines, i.e., immortal cell lines, which can be kept alive indefinitely in cell culture. These are especially tumor cells; the best-known non-immortalized cell culture was taken from a cervical carcinoma in 1951 and known by the name HeLa.

A distinction is made between cells which are propagated in suspension cultures and cells which grow in an anchoring-dependent manner, i.e., adherently. Suspension cells are, for example, lymphocytes which are present free-floating in the medium.

A primary culture refers to a non-immortalized cell culture which was obtained directly from a tissue of an organism. The cells are obtained by treating them with trypsin, for example, which breaks down the proteins maintaining the union of cells. Cells are therefore singularized. In a specific medium which also contains, inter alia, growth factors, they start to propagate through division.

The culture conditions for the individual cells differ considerably. What must be taken into account are specific media, pH, nutrient concentration, $CO_2$ content and other important parameters; these are known to a person skilled in the art and can be looked up in standard works. Depending on the division rate and density of the cells, the unions of cells are dissociated and they are distributed among new vessels; this process is called splitting or passaging. Since cells which grow too densely exhibit inhibition due to cell contact and no longer continue to grow, cells must be split regularly. This applies especially to cells which grow adherently (on surfaces), such as, for example, fibroblasts or endothelial cells.

Typical commercially available media for cell cultures of human origin are RPMI-1640, Dulbecco's Modified Eagle Medium and Ham's F12. For washing of cells, a person skilled in the art is familiar with balanced salt solution, Hanks' salts or Earle's salts.

Simple vessels for the culturing of cells can be Erlenmeyer flasks or Petri dishes made of glass or plastic. The vessels are filled with a certain volume of liquid medium, inoculated with cells and shaken for a certain period of time. However, these vessels have a limited surface area, meaning that cell growth is greatly limited. Furthermore, it is difficult to check and regulate culturing parameters such as pH and temperature directly in the vessel. To this end, a sample must be constantly taken, a process which always poses a risk of contamination because of the possible infiltration of disruptive pathogens such as fungi or bacteria. The change of medium is also associated with a risk of contamination, because the used medium must be removed using a pipette and the vessel must be replenished with fresh medium.

In the case of industrial use, for example in the production of cell cultures for vaccines or stem cells, closed cell-culture dishes or flasks having different structures for enlargement of surface area have therefore become established. Said enlargements of surface area are usually realized by ribs on which the cells can additionally grow. The cell-culture dish or flask is filled with liquid medium, inoculated with cells and moved by a vibrating, shaking or rocking apparatus so that growth medium washes around the cells as efficiently as possible and the cells can grow. However, in the case of cell-culture dishes or flasks as well, it is not possible to check and regulate culturing parameters directly in the vessel. The cell-culture dish or flask must be opened for sampling. So-called roller bottles have become established for the culturing of cell lines such as stem cells. These are round bottles made of glass or plastic with a lid that have a smooth or ribbed internal surface. They can be rotated continuously by means of a roller apparatus, with the result that medium continuously washes around the cells present inside. However, the internal structures for enlargement of surface area prevent medium from also reliably washing around all regions inside that are covered by cells. In these regions where medium does not wash around the cells, the cells grow more slowly or die.

Bioreactors or so-called fermenter systems are particularly reliable for culturing cells. These are containers, which are closable with a solid lid, in which medium and cells are present. Fermenters do not have any enlargements of surface area because the cells do not attach to the walls of the fermenter, but grow on microparticles. The uniform supply of medium is very important in a fermenter; in many cases, the lid has located therein a centrally arranged solid stirrer which, upon closure of the fermenter, dips into the liquid and moves or stirs medium and the cells present therein. The stirrer is usually a propeller stirrer or a paddle stirrer. Known fermenters have various inlets and outlets via which medium, gases or special nutrients are supplied. It is customary to check and regulate the culturing parameters such as pH and temperature directly in the vessel by means of probes. The disadvantage of these fermenters is that they are very expensive and are therefore not used as disposable items. Owing to the stirrer, which can also be attached to the base of the container, there is only limited space for internal structures for enlargement of surface area.

Further disadvantages of culturing in the fermenter are the shear forces which arise because of the stirrer. These arise depending on the stirring speed. This results in the problem that, if the stirrer speed is too low, homogeneous mixing and sufficient gas exchange are not ensured, but if the stirrer speed is too high, the cells are damaged because of the shear forces.

If the cells are to be detached from the microparticles, technical difficulties arise here as well. First, the cells must be detached from the carriers and then separated. If, for example, trypsin is used for the detachment, longer exposure times are necessary, and this can damage the cells. The cells must then be separated from the microparticles, and this represents a further process step with all the associated validation and investment costs.

An Archimedes' screw is a screw for moving or conveying solid or liquid material, said screw consisting of multiple turns and arranged spirally. The screw rotates around a solid central axis or a rod, forming multiple chambers. As a result of the rotation of the screw, all the chambers move toward the end of the screw and transport the solid or liquid material. The chambers are bounded above and below by, in each case, a blade section of the spiral. At the upper end of the screw, the material runs out of the vanishing chamber, and what is formed at the beginning of the screw is a new chamber which is filled with material from an inlet.

An Archimedes' screw is physically defined by the following variables: tube diameter of the solid central axis, the screw diameter, installation angle of the entire screw relative to the floor surface, the design head, difference in liquid levels, the maximum head, required hydraulic head, number of flights, length of bladed section, and pitch.

The Archimedes' screw is known from the prior art as a stirrer apparatus in bioreactors or fermenters, and it is either fixed in the base of the bioreactor as a permanently mounted component or it is attached to the lid. It ensures homogeneous mixing of the liquid volume, i.e., medium and cells present therein. The bioreactors are usually made of metal (stainless steel) or glass, and the Archimedes' screw is likewise made of metal so that simple cleaning or sterilization is possible. Bioreactors made in this manner are complicated and expensive to manufacture. They are not disposables. Since genetically modified cells are increasingly being used in biotechnology, there is an increased need for disposables. This dispenses with complicated cleaning procedures, and residues can be disposed of more easily and more safely.

Object

It is an object of the present invention to provide an improved cell-culture bottle for adherent cells which has a relatively large surface area for adherence of the cells and which makes it possible for medium to reliably wash around the cells during the growth period.

Achievement of the Object

This object is achieved according to the invention by an apparatus as claimed in claim 1. Advantageous embodiments of the apparatus can be gathered from the dependent claims.

The invention provides a novel cell-culture bottle 1 for adherent cells (e.g., human mesenchymal stem cells).

The cell-culture bottle 1 according to the invention comprises the following components:

The vessel 10 forms the outer shell of the cell-culture bottle 1. It preferably has a wall thickness of 0.1 to 1 mm and a diameter D of preferably 5 cm to 30 cm.

The vessel 10 is formed as one piece and has three subregions: a base region 12, a lid region 14, and a cylinder region 16 which is arranged between the base region 12 and the lid region 14. The cylinder region 16 is cylindrical. The vessel 10 has an opening in the lid region 14. The side of the cylinder region 16 that is facing the lid region is, by definition, the top side of the cylinder region. The side of the cylinder region 16 that is facing away from the lid region is, by definition, the bottom side of the cylinder region. The base region 12 is designed to be open or closed.

The cell-culture bottle 1 according to the invention comprises an Archimedes' screw 30 arranged in the cylinder region 16 of the vessel 10 and having a central tube 40 which is arranged along the central axis of said Archimedes' screw 30 and through which liquid is flowable and having at least one wall 50 which is arranged concentrically around the central tube 40. The central tube 40 serves to make it possible to introduce at least one probe for the monitoring of the growth conditions of the cells or to make it possible to introduce or remove fluid. The Archimedes' screw 30 forms multiple helical turns around the central tube 40. The Archimedes' screw 30 is integrally connected to the cylinder region 16 of the vessel 10 and to the at least one wall 50. Alternatively, multiple walls 50 can also be used (see the figure of FIG. 2). The Archimedes' screw 30 and the at least one wall 50 are integrally connected to one another. Furthermore, the Archimedes' screw 30 and the at least one wall 50 are arranged such that a fluid (e.g., medium or gas) can pass along the Archimedes' screw 30 from the bottom side of the cylinder region 16 into the lid region 14 of the vessel 10 when the cell-culture bottle 1 according to the invention rotates or is rotated.

Fluid (e.g., medium or gas) containing the cells to be cultured is introduced into the cell-culture bottle 1 according to the invention, more particularly into the cylinder region 16, so that, under suitable conditions, the fluid containing the cells is distributed inside the vessel 10, i.e., on the at least one wall 50, on the Archimedes' screw 30, on the central tube 40 and on the internal side of the vessel 10. These are the inner surfaces of the cell-culture bottle 1. The cells adhere to said inner surfaces and grow. Compared to known apparatuses, the at least one wall 50 and the Archimedes' screw 30 enlarge the inner surface area of the cell-culture bottle 1, with the result that more cells per bottle can adhere and grow inside the vessel 10.

The Archimedes' screw 30 fills the entire inner diameter of the vessel 10. The central tube 40 is arranged parallel to the wall of the cylinder region 16 and preferably has an outer diameter d of 0.5 to 2.0 cm. The inner diameter is preferably 0.48 cm to 1.98 cm. The central tube 40 can protrude from the lid region 12 of the vessel 10. A first opening 41 is located at the upper end of the central tube 40 on the top edge of the lid region 14. Alternatively, the first opening 41 is located in the region of the central tube 40 that protrudes from the lid region 12.

In an alternative embodiment of the cell-culture bottle 1 according to the invention, it additionally comprises in the lid region 14 a separate lid for closure and for avoidance of contamination during transport. Said lid is designed such that it can close the opening 41. To this end, the lid has a slightly larger diameter than the lid region 14 of the vessel 10, so that the connection between the vessel 10 and the lid is effected via a plug connection. Alternatively, the lid and the vessel 10 have threads, so that the connection between the vessel 10 and the lid is effected via screwing. The lid preferably has a filter which allows gas exchange, but provides protection against contamination, for example a sterile filter.

Furthermore, it is possible to connect the cell-culture bottle 1 according to the invention to a culturing system via the central tube 40 and the first opening 41, for example for the supply and discharge of fluid or cells. This is, for example, achieved by means of a hose system which is connected to the cell-culture bottle 1 according to the invention.

Furthermore, the central tube 40 has a second opening 42 inside the vessel 10 on the bottom side of the cylinder region. Through the first opening 41 or the second opening 42, fluid (e.g., medium or gas) containing the cells to be cultured can pass into the interior of the vessel 10 and also be removed.

The pitch of the Archimedes' screw is preferably 2 mm to 10 mm.

What is meant here by pitch is the distance between two planes of the Archimedes' screw 30. The pitch angle α of the Archimedes' screw 30 is preferably approx. 2° to 5°.

The cell-culture bottle 1 is filled with a certain inoculum of fluid (e.g., medium or gas) containing the cells to be cultured. This is preferably done via the central tube 40, so that fluid and cells can pass into the interior of the vessel 10 and can wet the inner surfaces thereof. In the process, the cells can settle on the concentric walls 50 and on the internal Archimedes' screw 30 and can use them as a growth surface. As a result of rotation of the cell-culture bottle 1, all regions of the interior of the vessel 10 are wetted and there is optimal mixing of the fluid (e.g., medium or gas) containing the cells to be cultured.

The vessel 10 preferably has an opening 11 in the lid region 14 beyond the central tube 40. Cells and used fluid (e.g., medium or gas) can be removed via this opening 11 of the vessel 10.

The preferred tilt angle β of the vessel 10 and hence of the Archimedes' screw 30 is between 150° and 60°, preferably less than 45°. A smaller tilt angle is advantageous in order to achieve the minimum fill level with less (often very expensive) fluid (e.g., medium). The angle can also be smaller than 30°; what is crucial is that fluid is conveyed into the interior of the vessel 10 upon rotation of the cell-culture bottle 1 and displaces gas in the process before it flows back through the central tube 40.

The layer thicknesses of the regions of the cell-culture bottle 1 according to the invention are preferably between 0.1 mm and 2.0 mm. The minimum or maximum possible layer thickness also depends on the manufacturing process. If the cell-culture bottle 1 according to the invention comprises multiple walls 50, the distance between them is preferably between 3 mm and 10 mm. A number of 2 to 16 walls has proven to be advantageous.

In a second embodiment of the cell-culture bottle 1 according to the invention, it additionally has a coating. Said coating is applied on the surface of the Archimedes' screw 30, the at least one wall 50 and/or the internal side of the vessel 10. It serves to make it possible for the cells to adhere better to the inner surfaces of the cell-culture bottle 1 and to colonize said surfaces as completely as possible. The coating comprises polysaccharides and/or peptides. Alternatively, the surface can be hydrophilized by means of a plasma.

In a third embodiment of the cell-culture bottle 1 according to the invention, it has a closed base region 12, meaning that the cell-culture bottle 1 is designed to be closed in the lower region. The base region 12 is integral with the cylinder region 16 and the lid region 14.

In a fourth embodiment of the cell-culture bottle 1 according to the invention, it has a rotation mechanism 60 for rotation of the vessel 10. The rotation mechanism 60 is, for example, a motor. It is attachable to the base region 12. The connection of the rotation mechanism 60 to the base region 12 is, for example, effected by means of at least one arbor, by means of at least one indentation or protrusion, or by means of magnets or similar fastening options. The rotation mechanism 60 is capable of rotating the vessel 10 containing the Archimedes' screw 30 at any speed, and so, when used with adherent cells and fluid inside the vessel 10, fluid washes around largest possible proportions of the inner surface in order to ensure optimal growth of the adherent cells.

In a fifth embodiment of the cell-culture bottle 1 according to the invention, it has at least one filter 70 in the central tube 40. The filter 70 is permeable to gases, but protects the interior of the cell-culture bottle 1 from contamination. For example, it is a sterile filter. It can be arranged directly in the central tube or any of the openings 11, 41, 42.

In a sixth embodiment, the central tube 40 has a third opening 43. It is located at the point of contact between the central tube 40 and the lid region 14 of the vessel 10. Said opening 43 serves as an overflow, so that fluid (e.g., medium or gas) containing the cells to be cultured can flow back into the base region 12 of the vessel 10 via the central tube 40 when said fluid reaches the lid region 14 of the vessel 10. In this embodiment, the opening 11 can be omitted.

Furthermore, it is possible to use the cell-culture bottle 1 according to the invention in a culturing system. The inflow and/or the removal of fluid (e.g., medium or gas) containing the cells to be cultured are effected via the central tube 40.

Within a culturing system, the cell-culture bottle 1 according to the invention performs the task of a disposable reactor or a disposable stirred reactor. This is advantageous for production processes involving shear-sensitive cells (suspension and adherent cultures) and pharmaceutical products, as well as for producing media, inoculum and mixing processes. The cell-culture bottle 1 according to the invention is designed as a disposable bottle.

The advantage of using disposable systems is the elimination of sterilization in place (SIP) and cleaning in place (CIP) and thus the reduction of process times. In addition, the risk of cross-contamination is reduced, and the complexity of qualification and validation of a process is reduced, which allows overall cost savings of up to 50%. There is no need for CIP validation for an external separation system.

During movement of the vessel 10 containing the Archimedes' screw 30, what takes place is movement and uniform exchange of fluid (e.g., medium or gas) containing the cells to be cultured, meaning that the cells are uniformly well supplied over the culturing period. This function corresponds to a stirrer in a stirred reactor. Through the internal vertical central tube 40, it is possible, from the outside in a simple and sterile manner, to introduce one or more measurement probes for measurement of temperature, pH, gas content or the like, to add fresh fluid or additional substances such as trypsin and/or to remove used fluid in order to monitor, measure, control and regulate the culturing process (i.e., cells and/or fluid). Outward and inward conduction of the fluid are performable in a temporally separated manner. The inward conduction of fresh fluid can be effected via a probe in the central tube 40, so that fresh fluid reaches the vessel 10 via the second opening 42 of the central tube 40. The removal of used fluid and/or cells can be effected via a second probe via the opening 11 in the lid region 14 or the opening 41. This arrangement allows automation of the culturing process. Cell propagation is distinctly increased with simultaneous savings in terms of materials and personnel. It is particularly advantageous that the arrangement of the components of the cell-culture bottle 1, which arrangement is according to the invention, requires a significantly lower inoculation density of cells to be cultured, because fluid reliably washes around the cells and a relatively large surface area is available for growth.

The culturing system preferably comprises yet further components:

A measurement device for capturing various parameters important for successful culturing of cells, for example pH, partial pressure of oxygen, partial pressure of $CO_2$ and temperature, as measurement data. Measurement devices can be, for example, a pH measurement probe, an oxygen probe, a temperature measurement probe and/or other measurement probes. The measurement of said parameters can be achieved via impedance spectroscopy. This makes it possible to monitor the cell count of the cell line, the vitality thereof and possibly production activity and to thus automate the entire course of culturing, meaning that an exact end of the culturing process is determinable.

The culturing system further comprises an evaluation device for evaluating the measurement data of the measurement device and for comparing them with reference data and for determining a deviation of the measurement data. To identify problems in the culturing of cells, the evaluation device particularly advantageously evaluates the measurement parameters together, with the result that reliability is increased and the likelihood of a malfunction due to a basis of insufficient measurement data is reduced. The transmission of the measurement data generated by the measurement device to an evaluation device can be effected via a cable connection or wirelessly.

The evaluation device preferably additionally comprises a database or access to a database or to stored reference data of the measurement data. The captured measurement data inside the cell-culture bottle 1 can then be compared with said reference data. The deviations are captured, stored or sent, for example, to a control unit which controls the overall process and counteracts malfunctions. Furthermore, the culturing system preferably comprises an output device for output of the measurement data measured by the measurement device and/or of the determined deviations in relation to the reference data.

The cell-culture bottle 1 according to the invention is preferably made of a material suitable for additive manufacturing, such as, for example, plastic, for example acrylonitrile butadiene styrene (ABS), acrylate styrene acrylonitrile (ASA), high-impact polystyrene (HIPS), thermoplastic elastomers (TPE), polycarbonates (PC), polylactides (PLA), polyethylene terephthalate (PET), polyethylene terephthalate glycol (PETG), polymethyl methacrylate (PMMA) or polyvinyl alcohol (PVA or PVOH). Alternatively, the material used is resin. According to ISO 4618:2014, resins are substances which are synthetically produced by polymerization, polyaddition or polycondensation reactions. According to the conventions of the IUPAC, these are soft solids or highly viscous substances which usually contain prepolymers having reactive functional groups. During processing, synthetically produced resins generally consist of two main components. Mixing of both parts (resin and hardener) results in a reactive resin compound. During curing, there is an increase in viscosity, and what is obtained after curing has been completed is an unmeltable plastic.

The cell-culture bottle 1 according to the invention is produced by means of additive manufacturing processes such as, for example, selective laser sintering (SLS)/selective laser melting, fused deposition modeling (FDM) and stereolithography (SLA/DLP). Said processes are known to a person skilled in the art. They make it possible to print overhangs and cavities without a support material having to be used and to be removed after printing. The processes mentioned are known to a person skilled in the art. Preference is given to producing the cell-culture bottle 1 according to the invention such that it is sterilized. There is already commercially available sterile material for FDM and the method is carried out under sterile conditions, meaning that the cell-culture bottle 1 according to the invention is produced in a sterile manner. In the case too of SLA and SLS, production results in a sterile bottle. Alternatively, the cell-culture bottle 1 according to the invention is only sterilized after manufacture, for example by means of gamma sterilization.

A method for culturing cells in a cell-culture bottle 1 according to the invention comprises at least the following steps:

a) filling the cell-culture bottle 1 with fluid (medium, liquid, gas)

b) adding the cells to be cultured to the cell-culture bottle 1 c) rotating the cell-culture bottle 1, so that the fluid is distributed and covers the cells, so that the cells can settle in the vessel 10, in the Archimedes' screw 30, on the at least one wall 50 and the central tube 40 and divide d) removing the fluid at a certain cell density e) adding a buffer to the cell-culture bottle 1 in order to wash the cells.

f) detaching the cells from the vessel 10, the Archimedes' screw 30, the at least one wall 50 and the central tube 40 g) stopping the detachment reaction by addition of fresh fluid h) removing the fluid containing detached cultured cells The filling of the cell-culture bottle 1 in step a) is done, for example, by means of a serological pipette, the cell-culture bottle 1 being filled with fluid via the central pipe 40 in such an amount that, upon rotation of the cell-culture bottle 1, the fluid is conveyed toward the lid region 14 such that the conveyed fluid within the Archimedes' screw displaces the gas remaining therein.

The removal of the fluid in step d) is done, for example, by means of a serological pipette. The buffer in step e) is, for example, PBS. It is highly suited to washing the cells. The detachment of the cells in step f) is done, for example, by means of a serological pipette by addition of trypsin or a comparable enzyme for detachment of the cells.

WORKING EXAMPLES

Working example 1: Use of the cell-culture bottle 1 according to the invention in standalone operation:

The cell-culture bottle 1 is filled in an aseptic environment (e.g., safety workbench) with a suitable fluid for the cells to be cultured and a starter culture composed of cells to be cultured. The cell-culture bottle 1 is then rotated by means of a rotation mechanism or placed onto a rotation apparatus. Such a rotation apparatus preferably comprises at least two rollers onto which the cell-culture bottle 1 is placed. The two rollers rotate, thereby causing the cell-culture bottle 1 lying thereon to rotate in the opposite direction. The rotation apparatus lies horizontally or preferably at an angle of inclination β of the vessel 10. A rotation speed appropriate for the cells is adjustable on the rotation apparatus. The rotation apparatus can be enclosed like an incubator, so that important parameters such as, for example, temperature, partial pressure of $O_2$ and partial pressure of $CO_2$ can be kept constant inside. The cells which are cultured are adherent cells, such as, for example, human mesenchymal stem cells. The duration of culturing varies depending on the cell type; in general, it lasts up to a certain cell density known to a person skilled in the art.

The removal of the cultured cells is known to a person skilled in the art and is done according to standard guidelines.

Working example 2: Use of the cell-culture bottle 1 according to the invention in a classic bioreactor, for example in an inclined bioreactor, instead of a stirrer.

Figure 5:
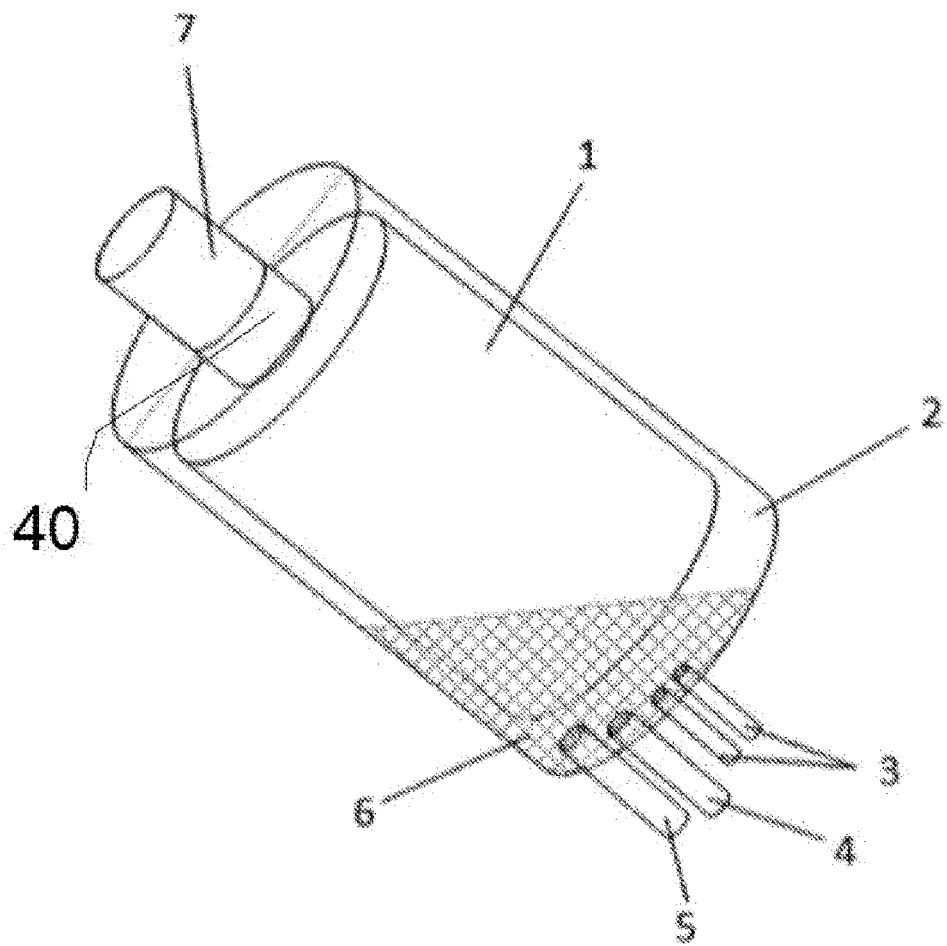

In this embodiment, the cell-culture bottle 1 is open in the base region 12, meaning that the blade of the Archimedes' screw 30 lies open. The entire cell-culture bottle 1 is located completely inside a reactor tank 2 of a bioreactor (see FIG. 5). Customary bioreactors and reactor tanks are known to a person skilled in the art. As is customary, the reactor tank 2 is filled with fluid and cells, heated and aerated so that the appropriate reaction conditions for the growth of the cells to be cultured are achieved. From the outside, the fluid and the cells to be cultured are supplied to the reactor tank 2 and discharged, and so, by rotation of the cell-culture bottle 1, fluid and cells also pass into the interior of the vessel 10. The cell-culture bottle 1 according to the invention performs the function of a stirrer inside the reactor tank 2. The reactor tank 2 is filled with fluid such that said fluid passes into the interior of the vessel 10 as a result of rotation of the bottle. The rotation is effected by attaching an external rotation mechanism to the cell-culture bottle 1, for example via the central tube 40. For example, it can be attached outside of the tank via a plug connection, as is customary in stirred tank reactors for the stirrer shaft (FIG. 5). The bioreactor is equipped with the probes 3 for pH, temperature, partial pressure of $O_2$, partial pressure of $CO_2$, etc., which probes are known to a person skilled in the art, and connected to a control system, for example a process control system. Furthermore, the culturing conditions in the reactor can be measured and readjusted at any time. The culturing ends when the desired cell density has been reached in the cell-culture bottle 1 according to the invention. The fluid is then removed from the reactor tank 2 and also from the interior of the cell-culture bottle 1 according to the invention and a suitable buffer such as, for example, PBS is added in order to wash the cells. Thereafter, while rotating the cell-culture bottle 1 according to the invention, an enzyme such as, for example, trypsin is added to the reactor tank 2 and the cell-culture bottle 1 according to the invention in order to detach the cells from the surface inside the cell-culture bottle 1 according to the invention. Afterwards, fresh fluid is supplied to the reactor tank 2 and the cell-culture bottle 1 according to the invention, so that the cells are present in a suspension and can be harvested for the later anticipated application.

FIGURE LEGENDS AND LIST OF REFERENCE SIGNS

FIG. 1 shows, by way of example, one embodiment of the cell-culture bottle 1 according to the invention. Here, the closed base region 12 shown is optional. Furthermore, the third opening 43 of the central tube 40 is optional.

Figure 2:
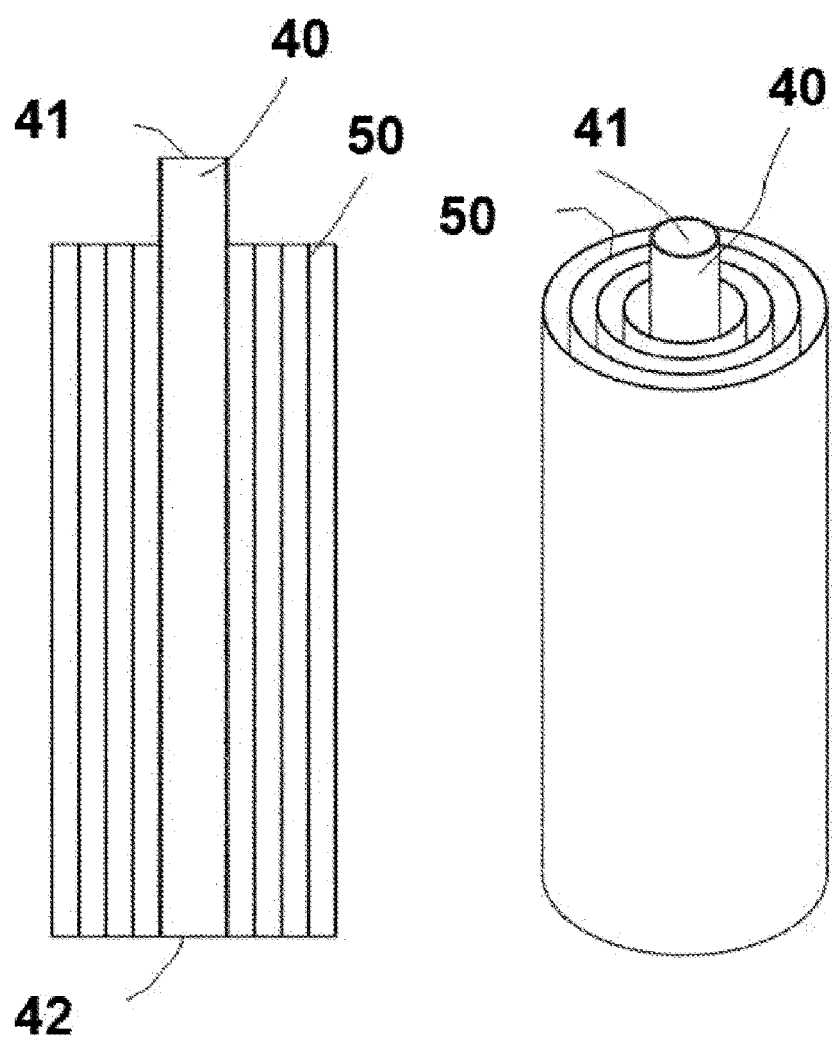

FIG. 2 shows an exemplary arrangement of multiple walls 50 around the central tube 40.

The remaining components of the cell-culture bottle 1 are not shown in this figure for the sake of clarity.

FIG. 3 shows, by way of example, in a side view, FIG. 3a, an Archimedes' screw 30 having a central tube 40. FIG. 3b displays the longitudinal section.

Figure 4:
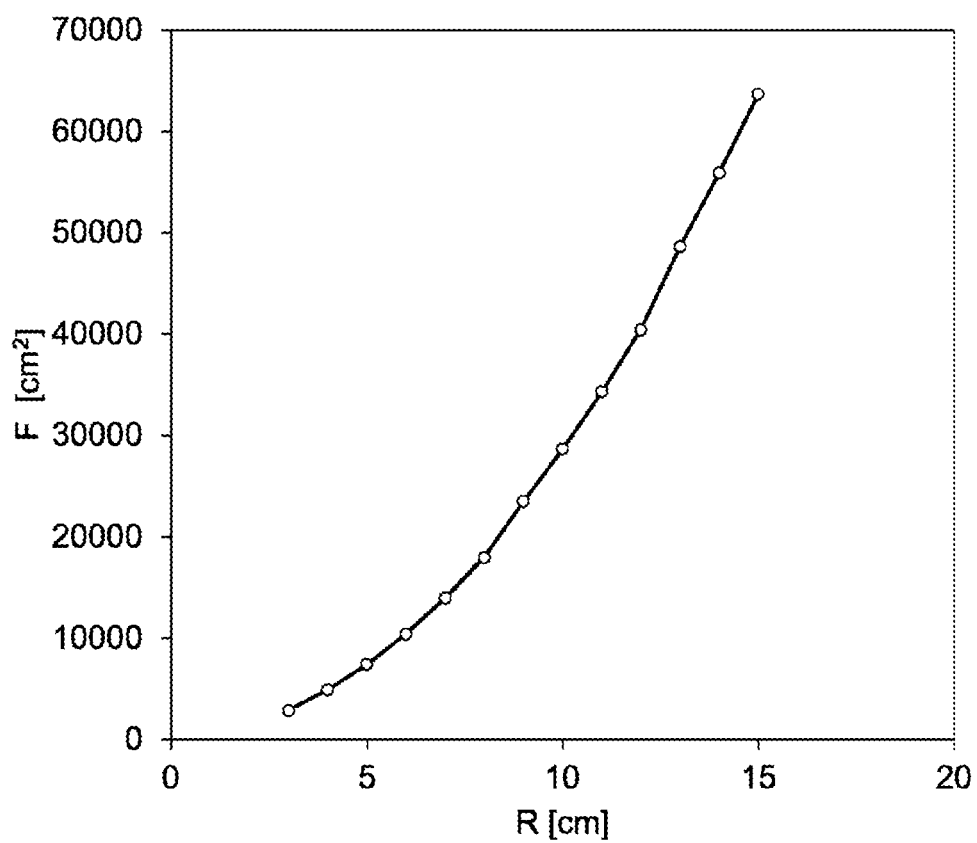

FIG. 4 shows how much the growth surface area F in the vessel 10 increases in relation to the radius R of the vessel 10. In this example, the cylinder region 16 has a height of 16 cm to 20 cm and comprises 20 turns, with a distance of 0.8 cm between the walls 50.

FIG. 5 shows the use of the cell-culture bottle 1 according to the invention instead of a stirrer in an inclined classic bioreactor.

LIST OF REFERENCE SIGNS 1 cell-culture bottle
2 reaction tank
3 probes
4 inflow
5 outflow
6 fluid
7 rotation mechanism of the stirred tank reactor
10 vessel
11 opening of the vessel 10
12 base region
14 lid region
16 cylinder region
30 Archimedes' screw
40 central tube
41 first opening of the central tube 40
42 second opening of the central tube 40
43 third opening of the central tube 40
50 wall
α angle of inclination of the Archimedes' screw 30
β angle of inclination of the vessel 10
D diameter of the vessel 10

The invention claimed is:

1. A cell-culture bottle comprising
a vessel comprising three subregions: a base region, a lid region and a cylinder region arranged therebetween,
an Archimedes' screw arranged internally in the cylinder region of the vessel and having a central tube which is arranged along the central axis of said Archimedes' screw and through which liquid is flowable,
at least one wall which is arranged concentrically around the central tube and which extends over the entire cylinder region of the vessel,
wherein the cell-culture bottle is formed as one piece and wherein the central tube is designed such that it has a first opening on the outer side of the vessel in the lid region and has a second opening inside the vessel on a bottom side of the cylinder region and wherein the Archimedes' screw is integrally connected to the cylinder region of the vessel and to the at least one wall, wherein the Archimedes' screw and the at least one wall are arranged such that a fluid can pass along the Archimedes' screw from the bottom side of the cylinder region into the lid region of the vessel upon rotation of the cell-culture bottle.

2. The cell-culture bottle as claimed in claim 1, wherein the vessel has an opening in the lid region beyond the central tube.

3. The cell-culture bottle as claimed in claim 1, wherein the cell-culture bottle has a coating comprising polysaccharides and/or peptides, wherein said coating is applied on a surface of the Archimedes' screw, the at least one wall and/or an internal side of the vessel, so that cells can adhere to the inner surfaces of the cell-culture bottle and grow thereon.

4. The cell-culture bottle as claimed in claim 1, further comprising a closed base region, meaning that the cell-culture bottle is designed to be closed on the bottom side of the cylinder region, wherein the base region is integrally connected to the cylinder region.

5. The cell-culture bottle as claimed in claim 1, wherein the cell-culture bottle has a rotation mechanism for rotation of the vessel, wherein said rotation mechanism is attachable to the base region of the vessel.

6. The cell-culture bottle as claimed in claim 1, wherein the cell culture bottle has a filter in the central tube.

7. The cell-culture bottle as claimed in claim 1, wherein the central tube has a third opening, wherein said third opening is located at a point of contact between the central tube and the lid region of the vessel, so that fluid can get from the base region to the lid region of the vessel via the Archimedes' screw and can, via the third opening into the central tube 40, flow back to the bottom side of the cylinder region of the vessel.

8. The cell-culture bottle as claimed in claim 1, wherein the cell-culture bottle is made of a material suitable for additive manufacturing.

9. The cell-culture bottle as claimed in claim 8, wherein the material is selected from the group consisting of acrylonitrile butadiene styrene (ABS), acrylate styrene acrylonitrile (ASA), high-impact polystyrene (HIPS), thermoplastic elastomers (TPE), polycarbonates (PC), polylactides (PLA), polyethylene terephthalate (PET), polyethylene terephthalate glycol (PETG), polymethyl methacrylate (PMMA) or polyvinyl alcohol (PVA or PVOH).

10. A culturing system, comprising a cell-culture bottle as claimed in claim 1.

11. A method for culturing cells in a cell-culture bottle as claimed in claim 1, comprising at least the steps of:
  a) filling the cell-culture bottle with fluid;
  b) adding the cells to be cultured to the cell-culture bottle;
  c) rotating the cell-culture bottle, so that the fluid is distributed and covers the cells, so that the cells can settle in the vessel, in the Archimedes' screw, on the at least one wall and the central tube and divide;
  d) removing the fluid at a certain cell density;
  e) adding a buffer to the cell-culture bottle in order to wash the cells;
  f) detaching the cells from the vessel, the Archimedes' screw, the at least one wall and the central tube;
  g) stopping the detachment reaction by addition of fresh fluid; and
  h) removing the fluid containing detached cultured cells.

* * * * *